United States Patent

Login et al.

[11] 4,395,373
[45] Jul. 26, 1983

[54] PHOSPHATED AMINE OXIDES

[75] Inventors: Robert B. Login, Media; Pa.

[73] Assignee: Jordan Chemical Company, Folcroft, Pa.

[21] Appl. No.: 251,851

[22] Filed: Apr. 7, 1981

[51] Int. Cl.³ .............................................. C07F 9/09
[52] U.S. Cl. .................................... 260/928; 260/945;
260/980; 260/124
[58] Field of Search .................... 260/928, 945, 980

[56] References Cited
U.S. PATENT DOCUMENTS 3,210,192 10/1965 Willems et al. ...................... 260/945
3,429,914 2/1969 Crutchfield et al. .............. 260/502.5
3,692,881 9/1972 Stanford et al. ...................... 260/980

Primary Examiner—Anton H. Sutto
Attorney, Agent, or Firm—Robert S. Lipton

[57] ABSTRACT

Phosphated amine oxides of the formula

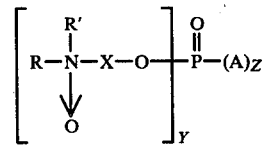

wherein R and R', which may be the same or different, are alkyl, alkenyl, or alkoxy of from 2 to 24 carbon atoms, R' may be further selected from the same group as X with the requirement that said group terminate in a hydroxyl or phosphate ester, X is a polyalkoxide of the formula

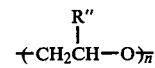

Wherein
R'' is hydrogen, $C_1$ to $C_{20}$ alkyl, or methylene alkoxy wherein the alkoxy chain is from $C_1$ to $C_{20}$, and phenyl N is an integer from 1 to 50

Y and Z are integers from
1 to 2 such that when Y is
2, Z is 1 and vice versa,

A is—OM wherein M is hydrogen, alkali metals, alkaline earth metals or quaternary ammonium counterions.

15 Claims, No Drawings

PHOSPHATED AMINE OXIDES

BACKGROUND OF THE INVENTION

The present invention describes novel compositions of matter consisting of molecules containing an amine oxide and phosphate ester as part of the same compound. Although, amine oxide and phosphate ester containing molecules as distinct compounds are known in the prior art, the combination of these two functional groups on the same molecule has not been disclosed or suggested. The literature describing the preparation of fatty alkyl based amine oxides and phosphate esters is both extensive and well known to those of ordinary skill in the art of surfactant manufacture and use; therefore it need not be reviewed. References to fatty alkyl based molecules with tertiary amine oxide and the salts of covalently bound acid groups on the same molecule are much less evident. For example Engelmann (U.S. Pat. No. 2,159,967) teaches the preparation and use of tertiary amine oxide carboxylates and sulfonates separated by 1 to 4 carbon atoms. Ulrich (U.S. Pat. No. 2,185,163) describes a rather ill defined tertiary amine oxide polyethoxylate subsequently sulphonated. Cahn and Kaniecki (U.S. Pat. No. 3,267,135 and 3,359,208 amongst others) teach the preparation and use of N-(2-hydroxyalkyl-)N-Methyltaurine-N-oxides. Stanford and Vogelsang (U.S. Pat. Nos. 3,477,956; 3,692,881; 3,728,419 and 3,787,534,) teach the preparation and use of phosphated hydroxy amines but do not mention or suggest conversion of the subsequent tertiary amine phosphate ester salt into an amine oxide derivative.

Tertiary amine oxides when acidified to low pH exist as cationic materials with three alkyl and one hydroxyl substituents; therefore, they can be considered under these conditions as quaternary ammonium derivatives. Surfactant molecules containing both quaternary ammonium and phosphate esters on the same molecule are known. For example, Verdicchio (U.S. Pat. No. 4,132,657) teaches the preparation of complex phosphate ester surfactants derived from a quaternary dihydroxy compound. Mayhew (U.S. Pat. No. 4,209,449) describes phosphate quaternaries prepared by the interaction of the tiglycidyl ester of mono sodium phosphate and selected tertiary aminoamides. Similiar chemistry is disclosed by Lindemann et. al. (U.S. Pat. No. 4,215,064) dealing with selected mono and di glycidyl phosphate ester quaternizing agents and their reaction with a variety of selected fatty tertiary amines. Similiar reactions were originally described however by Shen (U.S. Pat. No. 3,304,349) who teaches the preparation in general of acid containing glycidyl ethers and their reaction into tertiary amines to form amphoteric or Zwitterionic fatty based surfactants.

Phosphorus may be in other oxidation states. For example Diery (U.S. Pat. No. 3,856,893) is the first of a series (U.S. Pat. No. 3,888,978; 3,922,344 and 3,928,509) teaches the reaction of 1,3-dioxa-2-phosphorinanes with various tertiary amines to form hybrid ionic phosphorus compounds containing phosphate and quaternary ammonium salts attached to the same molecule.

Organo-phosphono-amine oxide compounds are disclosed by Crutchfield and Irani (U.S. Pat. No. 3,429,914 and 3,483,178). They are prepared from amines, aldehydes and phosphorus acid. The condensation product of this reaction is then converted to an amine oxide with for example hydrogen peroxide.

The phosphated amine oxide compounds of the present invention exhibit outstanding foaming, wetting, cleansing, viscosity-building, emulsification, lubricity and antistatic properties; therefore, they are of excellent utility in many industrial applications requiring surface active agents. Unlike the amine oxides, the phosphated derivatives resist loss by volatility from hot surfaces. This property allows these novel compounds to function as fiber processing aids where the processes call for high temperature exposure. In addition the greatly reduced volatility eliminates the change of atmospheric pollution.

The multiplicity of ionic charge of these compounds also allows them to function as surfactants in the presence of strong electrolytes such as sodium hydroxide. This affords foam generation in the presence of strong electrolytes which is a desireable aid in cleaning. Foam stabilization is also achieved with selected candidates.

THE INVENTION

Phosphated amine oxides are prepared from hydroxyalkylamines of the following structure:

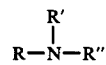

wherein R and R, which may be the same or different, are alkyl, alkenyl, or alkoxy of from 5 to 24 carbon atoms each or R and $R^1$ may also form a cyclic structure and be attached together; R'' is a polyalkoxy group of the following formula:

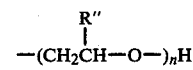

wherein R'' is hydrogen, methyl, ethyl, phenyl, or $C_1$ to $C_{20}$ alkoxy n is an integer from 1 to 50; in addition R' may be the same as R'' which results in a (bis—hydroxyalkyl) fatty amines. Such hydroxyalkyl fatty amines are well known and commercially available from several manufacturers. For example, they are readily manufactured from the corresponding fatty alkyl primary and secondary amines upon condensation with alkoxides such as ethylene oxide, propylene oxide, butylene oxide, $C_8$–$C_{25}$ alpha olefia oxides, and styrene oxide. In short all epoxide compounds reactive with fatty alkyl amines, affording hydroxyalkyl fatty amine derivatives. Typical examples are the Ethomeens available from Armak. These are based on coco, soya and tallow which indicate known fatty carbon chain length mixtures. The fatty amines are ethoxylated by well-known methods to whatever chain length of oxide that is desired. Although the above commercial products are ethoxylates, the nature of the oxide chain can be varied by use of other oxides such as propylene, butylene, styrene or $C_8$–$C_{25}$ alpha olefin epoxides or mixtures with each other and ethylene oxide. Addition of propylene or butylene oxide in admixture with ethylene oxide will result in a more hydrophobic hydroxy alkylamine, whereas styrene oxide will result in a more rigid structure.

The reaction of epichlorphydrin with fatty alcohols to form glycidyl ethers is another method of forming a alkyl epoxides suitable for the formation of hydroxyalkyl fatty amines.

The structure of the hydroxyalkyl fatty amine will have a major affect on the nature of the subsequently prepared phosphated amine oxide.

As the R group is changed to more lipophilic structure; for example, as the alkyl chain is increased from $C_8$ to $C_{18}$, the surfactant nature of the phosphated amine oxide will change. At one optimum chain length, detergency will be maximized. Classically with other types of surfactants; i.e. alcohol ethoxylates, amine oxides or phosphate esters the $C_{12}$–$C_{14}$ alkyl chain range is associated with maximum detergency. Smaller chain lengths will improve such properties as anti-static propersity, solubility in alkali or salt solutions and compatibility. Increasing the alkyl chain will improve solubility in oils and improve the ability of the phosphated amine oxide to work as a textile softener. The nature of the R'' alkoxide group will also affect the properties of the subsequently prepared phosphated amine oxide. Increasing the length of the oxide chain when prepared from ethylene oxide will result in greater water dispersibility or solubility. Increasing the amount of ethylene oxide also makes the alkoxylated amine more compatible as a starting material with the reagents needed to complete the conversation to phosphated amine oxide.

Once the properties desired in the phosphated amine oxide are determined and the best suited hydroxyalkyl fatty amine obtained, then the hydroxyalkyl fatty amine is converted into a phosphate ester with phosphorus pentoxide. Phosphorus pentoxide is much superior to polyphosphoric acid and much more reactive to hydroxyl terminals on hydroxyalkyl fatty amines. The reason for this is based on the ability of the tertiary amine to neutralize the acid groups on the polyphosphoric acid polymer rendering it anionic and much less reactive to hydroxyl groups. Phosphorus pentoxide is neutral and is not affected by the tertiary amine neutralization reaction. Thus much greater formation of phosphate ester occurs with phosphorus pentoxide than with polyphosphoric acid. In fact, because of the desireability of forming oligomeric materials with N,N-bis(hydroxyethyl)-fatty amines, phosphorus pentoxide and not polyphosphoric is the reactant of choice. Even if polyphosphoric acid were more reactive, its reaction with alcohols to form primary phosphate esters indicates that it would not have any value as a crosslinking agent.

Therefore, although a large number of N-hydroxyalkyl amines are available or can be synthesized, only those poly(N-hydroxyalkyl)amines such as the N,N-bis(hydroxyethyl)fatty amines can because of their multiplicity of hydroxyl groups enter into crosslinking reactions with phosphorus pentoxide to produce oligomeric products. These materials have the general formula

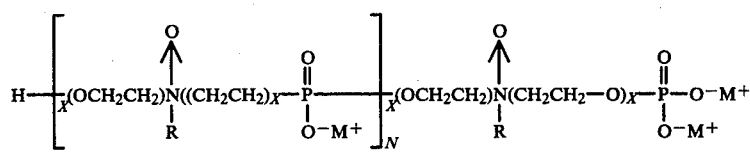

wherein n is an integer from 1 to 10 and R is a alkyl, alkenyl or alkoxy group of from 5 to 24 carbon atoms or aryl or alkylaryl of up to 20 carbon atoms. X is an integer from 1 to 50. X reflects the relative ease at which ethylene oxide can be added to N,N-bis(hydroxyethylamines) to form long chain polyethoxylates.

More specific examples of Phosphated Amine oxide compounds within the disclosure of the general formula given above are:

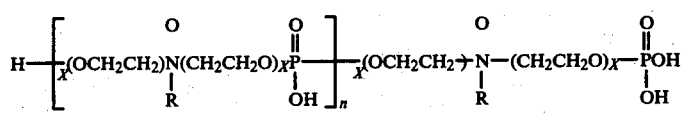

Wherein
R is selected from alkyl, alkenyl or alkoxy groups containing from 5 to 24 carbon atoms, or aryl or alkylaryl of up to 20 carbon atoms,
N is an integer from 1 to 10,
X is an integer from 1 to 50
$M^+$ is a cation selected from hydronium, alkali and alkaline earth metals or quaternary ammonium counterions.

Another example is a mixture such as:

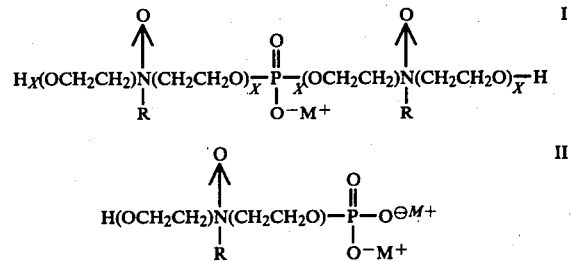

Wherein the ration of I to II is from about 1 to 1; to about 1 to 2, and the values for R,N,X and $M^+$ are the same as in the preceding formula.

It would be apparent to those skilled in the art of the preparation of phosphate esters to avoid any contamination with moisture or with low molecular weight mono functional materials; therefore, all precautions to use pure and dry N,N-bis(hydroxyethyl)fatty amines should be taken.

After the addition of $P_2O_5$, as the phosphation proceeds, the viscosity of the subsequent product increases to levels that are difficult to stir. This indicates crosslinking and chain extension. Under such circumstances a solvent can be employed that is relatively unreactive to $P_2O_5$. For example, tertiary butanol and triethyl phosphate can be used with good results. In fact, these solvents have the added benefit of being water soluble. Solvents however, are not desirable in products to be used in food, cosmetic or pharmaceutical applications.

The course of the phosphation reaction is followed by titration for acid number. When this value ceases to increase with time the reaction is considered to be complete. The phosphated N,N-bis(hydroxyalkyl)fatty amine oligomers can be further characterized by hydroxyl number. Thus, although the actual product is by nature a complex mixture of mainly primary and secondary phosphate esters of a mixture N,N-bis(hydroxyalkyl)fatty amines, the resulting phosphated ester oligomer can be identified reproduceably.

The phosphated N,N-bis(hydroxyalkyl)fatty amine oligomer is quite acidic and therefore, the tertiary amine groups are in their protonated form. They are relatively unreactive when thus protonated. Neutralization with bases such as sodium hydroxide, potassium hydroxide, alkali and alkaline earth hydroxides and carbonates to a pH of approximately 7 to 9 frees the amine so that it can be alkylated with typical quaternizing agents such as diethyl sulfate, dimethyl sulfate, ethylene oxide, methyl halides and so on; moreover, the tertiary amine can also react with hydrogen peroxide to form a phosphated amine oxide oligomers. Typically the phosphated N,N-bis(hydroxyalkyl)tertiary fatty amine oligomer is mixed with enough dilute base to form a 35–45% aqueous solution or dispersion which is between pH 7 and 9. A small quantity (0.1 to 5% of the mixture) of iron chelating agent such as diethylene triamine pentaacetic acid salt is added to prevent iron induced decomposition of hydrogen peroxide. This is followed by the addition of sufficient 35% hydrogen peroxide to effect amine oxide formation.

The following examples are presented to illustrate the invention, with parts and percentages by weight being used unless otherwise indicated.

EXAMPLE 1

In a suitable reaction vessel about 305 parts of N,N-bis-(hydroxyethyl)tallow amine was charged. After heating to 50° C., 85 parts of $P_2O_5$ was added slowly over 1.5 hrs. During the addition of $P_2O_5$, an exotherm was observed reaching 80° C. After another hour, the mixture had become too viscous to efficiently stir. 165 ml. of tert-butanol was slowly added in small aliquots over the next two hours to thin the reaction mixture. The final product was a uniform viscous liquid exhibiting an acid value of 156.

407 parts of the above phosphate ester was mixed with 90.5 parts of 25% NaOH. The partially neutralized phosphated fatty amine was further diluted with a mixture of 1 part pentasodium salt of diethylenetriaminepentaacetic acid (Na 5 DTPA) and 373 parts water. This was followed by heating to 70° C. and dropwise addition of 128 parts 35% $H_2O_2$ over ½ hr. An exotherm from 70° to 85° C. was observed during $H_2O_2$ addition. Temperature was maintained at 70° C. for 3 more hours.

The product was found to be in two phases because the pH was low. The ambient pH of the phosphated amine oxide was 5. Adjustment to pH 6.5 with 25% NaOH resulted in the formation of a uniform dispersion stable to splitting. Further adjustment of the pH to the alkaline side results in a dramatic increase in viscosity. An aliquot sufficient to form a 1% solution when added to water will readily disperse without building viscosity. Upon addition of caustic to increase pH above 7, the mixture turns transparent and thickens to form gel structures similar in appearance to those formed by high molecular weight polyethylene oxide polymers such as those sold under Polyox ® (UCC) brand.

EXAMPLE 2

In a suitable reaction vessel about 422 parts (1 mole) of the reaction product of coconut amine plus 5 moles of EO (Ethomeen C/15, Armak) was charged and heated to 60° C. 78 parts (1.1 equivalents) $P_2O_2$ was added slowly over one hour resulting in an exotherm to 85° C. The mixture was slowly heated to 100° C. in another hour then held at 100° C. for an hour. Acid number was 106 and hydroxyl number was 51.

180 parts of the above was mixed with a mixture consisting of 27.2 parts 25% NaOH, 1 part Na5DTPA and 240 parts water. This homogenous viscous mixture was heated to 60° C. 40 parts of 35% $H_2O_2$ was added over ½ hr which resulted in a modest exotherm to 66° C. The reaction mixture was held one hour at 65° C. which resulted in a 37.4% solids, viscous clear product (Jorphox C-15, a product of the Jordan Chemical Company) with a Gardner color of 4, 0.38% free $H_2O_2$, 7.9% free amine.

When added to anionic surfactants such as sodium lauryl sulfate, the above product would thicken the mixture while retaining product clarity and without compromising foaming ability.

EXAMPLE 3

In a suitable reaction vessel about 645 parts (1 mole) of the reaction product of coconut amine plus 10 moles of EO (Ethomeen C/20, Armak, was charged and heated to 60° C. 78 parts (1.1 equivalents) of $P_2O_5$ was added with good agitation over ½ hr. which resulted in an exotherm to 90° C. After two hours at 80°–90° C., the viscous mixture was heated to 90°–100° C. and held there for another hour. Acid number was 93 and hydroxyl number was 20.

262 parts of the above was mixed with a mixture consisting of 34.8 parts of 25% NaOH, 1 part Na5DTPA and 304 parts water. The uniform mixture was heated to 60° C. and 40 parts of 35% $H_2O_2$ added over 178 hr. This resulted in an exotherm to 80° C. The clear straw colored product was held at 75° C. for another 1.5 hrs. and decanted. This product was given the designation Jorphox C-20 (a product of the Jordan Chemical Company). It exhibited 42.5% solids, Gardner color 4, pH 6.2 free peroxide 0.17%, free amine 3.9%.

Addition of Jorphox C-20 to anionic surfactants such as sodium lauryl sulfate results in transparent but thickened products.

EXAMPLE 4

In a suitable reaction vessel about 5,700 parts of N,N-bis(hydroxyethyl)coco amine (Ethomeen C/12, Armak) was charged. At 20° C., the entire 1,700 parts of $P_2O_5$ powder was charged. With the aid of a high torque motor, this mixture was thoroughly stirred. Within one hour, the mixture had turned from a thin milky appearance into a brown clear and thick liquid. An appreachable exotherm was evident, within two hours, the mixture was at 155° C. and was unstirrable. It was allowed to cool for another hour at which time it was at 90° C. Upon cooling to ambient, the phosphated N,N-bis(hydroxyethyl)coco amine was a tough brittle solid exhibiting an acid value to 244. It could be broken up into chunks which were added to 4,400 parts of 25% KOH. After several hours of stirring at 60°–70° C., the chunks had dispersed to form a uniform solution with a pH between 7 and 9. To this mixture was added 14 parts Na5DTPA iron chelator followed by the slow addition of 2,200 parts 35% $H_2O_2$ to the mixture which was heated to 75°–85° C. After $H_2O_2$ addition, the high solids product was adjusted with DI water and dilute HCl to 35% solids and pH 7–8.

This particular product is commercially available under the Jorphox KCAO brand of the Jordan Chemical Company.

EXAMPLE 5

In a suitable reaction vessel was charged 3,050 parts of N,N-bis(hydroxyethyl)tallow amine (Ethomeen T/12, Armak) followed by 850 parts of $P_2O_5$. With the aid of a high torque turbine stirrer the mixture was rapidly stirred and homogenized before it reacted far enough to set up into a tough hard plastic mass. During this process and exotherm of 50°–70° C. was observed. Upon cooling, the product exhibited an acid value of 168.

The mixture was divided and one part was dissolved in 25% NaOH while another was dissolved in 25% KOH to form in both cases solutions in the pH 7–9 range. In both cases, the amount of base was close to that calculated based on neutralization of the acid value.

To each solution was added with stirring at 75°–85° C. 1.1 moles of 35% $H_2O_2$. This usually required 2–3 hrs in order to avoid excessive foaming and exotherm. The final product was diluted to the required 33–35% solids range with DI water and if needed a small amount of dilute HCl to adjust pH into the 7 to 8 range.

Products of the above type are commercially available under the Jorphox TAO (Na+ salt of tallow amine oxide-phosphate ester), Jorphox KTAO (K+ salt of the above).

Other compounds of the instant invention which can be prepared according to the procedures as illustrated by the foregoing examples include the following:

EXAMPLE 6

The reaction product of one mole of the 10 mole ethoxylate of soya amine and one mole of $P_2O_5$ subsequently neutralized with 25% KOH to pH 7 to 9 and converted to the corresponding amine oxide with 1.1 moles of 35% $H_2O_2$.

EXAMPLE 7

The reaction product of one mole of the 50 mole ethoxylate by hydrogenated tallow amine and one mole of $P_2O_5$ subsequently neutralized with 25% KOH to pH 7 to 9 and converted to the corresponding amine oxide with 1.1 moles of 35% $H_2O_2$.

EXAMPLE 8

The reaction product of one mole of the 15 mole ethoxylate of tallow diamine and one mole of $P_2O_5$ neutralized with 25% KOH to pH 7 to 9 and converted to the corresponding amine oxide with 2.2 moles of 35% $H_2O_2$.

EXAMPLE 9

The condensate of one mole of lauric acid and one mole of triethylene tetramine plus 20 moles of ethylene oxide reacted with one mole of $P_2O_5$ and subsequently neutralized with 25% KOH to pH 7 to 9 and converted to the corresponding amine oxide with 3.3 moles of 35% $H_2O_2$.

EXAMPLE 10

The condensate of two moles of stearic acid and one mole of triethylene tetramine plus 10 moles of ethylene oxide reacted with one mole of $P_2O_5$ and subsequently neutralized with 25% KOH to pH 7 to 9 and converted to the corresponding amine oxide with 2.2 moles of 35% $H_2O_2$.

EXAMPLE 11

The reaction product of one mole of the 10 mole ethoxylate of lauryl amine and one mole of $P_2O_5$ subsequently neutralized with tetramethylammonium hydroxide to pH 7 to 9 and converted to the corresponding amine oxide with 1.1 moles of 35% $H_2O_2$.

The compositions of the invention have general utility as surfactants. For example table 1 illustrates a simple comparison used by formulators of shampoos to determine foam stability. This test consists of adding 25 ml of a 0.1% solution of a mixture of sodium lauryl sulfate and a foam stabilizer to a stoppered 100 ml graduated cylinder which is then inverted rapidly five times. The results indicate the superior foam stabilization obtained with example 4 versus an analogous unphosphated amine oxide.

TABLE I

| Sample | Conc. % | Sodium Lauryl Sulfate* Conc. % | Cloud Point °F. | D.I. $H_2O$ - 1% sol'n Int. | 30' |
|---|---|---|---|---|---|
| Control | 0 | 12 | 76 | 70 | 45 |
| Control | 0 | 15 | 79 | 80 | 55 |
| Jorphox KCAO | 0.9 | 12 | 61 | 90 | 80 |
| Jorphox KCAO | 0.9 | 15 | 62 | 98 | 90 |
| Aromox** | 0.9 | 12 | — | 75 | 55 |
| C/12-W | 0.9 | 15 | — | 85 | 65 |

*P & G Equix S
**Abstracted from Armak literature

Jorphox KCAO (Example 4) also exhibits solubility in 25% caustic and performs as a wetter by the Draves test as illustrated in table 2.

TABLE 2

| Wetting (Draves Test): | | |
|---|---|---|
| | Time in Seconds | |
| Sample | 0.5% | 0.25% |
| CAO* | 7 | 13.5 |
| KCAO | 15 | 21.5 |

*Na salt analog of Example 4

Several of the products prepared according to this general procedure have exhibited unusual and remarkable properties. For example, the phosphated amine oxide based on bis(hydroxyethyl)tallow amine, Jorphox T-12 (a product of the Jordan Chemical Company) is dispersible in water at pH's below 7; however, above 7 the product is transformed into a remarkably effective thickener. One percent or less can be enough to gel water. The gel is not shear stable because the surfactant concentration is transferred into a very strong foam (lather) which can persist for hours. Products prepared from the ethoxylated bis(hydroxyethyl)cocoamines (Jorphox C-15 and C-20 products of the Jordan Chemical Company) exhibit strong thickening properties in combination with anionic surfactants such as sodium lauryl sulfate and selected C14-16 alpha olefin sulfonates. This is desirable for the preparation of gel like or concentrated shampoos. In fact, the combination of a phosphate and amine oxide on the same molecule is desirable from a formulator's point of view because phosphate ester based surfactants are usually excellent emulsifiers, detergents and wetting agents whereas amine oxide based surfactants are excellent foam boosters and stabilizers, and emollients. Both types of surfactants are excellent antistats; however, the amine oxides are volatile on hot surfaces; combination with a phosphate ester on the same molecule therefore results in the elimination of the volatility problem. This suggested the use of these products as temperature stable antistats. Evaluation of these materials in synthetic fiber spin finish formulations as an antistat component has given excellent results.

The phosphated amine oxide surfactants of the instant invention are being considered for a variety of surfactant applications. Amongst these are as antistats, conditioners and softeners for textile fibers and human hair, as thickeners, emulsifiers, foaming agents and foam stabilizers and boosters, as detergents, corrosion inhibitors, ore floatation aids, degreasers, scours, wetting agents, dispersing agents, chelating agents for example.

We claim:

1. Phosphated Amine Oxides Compounds of the formula

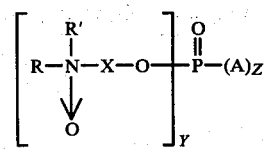

Wherein R and R', which may be the same or different are alkyl, alkenyl, or alkoxy groups containing from 5 to 24 carbon atoms, R and R' may also form a cyclic structure and be attached together, R' may be further selected from the same group as X with the requirement that said group terminate in a hydroxyl or phosphate ester, X is a polyalkoxide of the formula

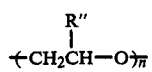

Wherein
R'' is hydrogen, $C_1$-$C_{20}$ alkyl, $C_1$-$C_{20}$ alkoxy, phenyl,
n is an integer from 1 to 50
Y and Z are integers from
1 to 2 such that when Y is
2, Z is 1 and vice versa,
A is —OM wherein M is hydrogen, alkali metals, alkaline earth metals or quaternary ammonium counterions.

2. Phosphated Amine oxide compounds of the formula

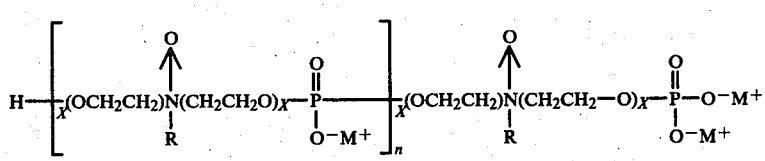

Wherein

R is selected from alkyl, alkenyl or alkoxy groups containing from 5 to 24 carbon atoms or aryl or alkylaryl of up to 20 carbon atoms,
N is an integer from 1 to 10,
X is an integer from 1 to 50
$M^+$ is a cation selected from hydronium, alkali and alkaline eath metals or quaternary ammonium counterions.

3. Phosphated Amine Oxide compounds as claimed in claim 2 wherein R has a coco alkyl distribution.

4. Phosphated Amine Oxide compounds as claimed in claim 2 wherein R has a tallow alkyl distribution.

5. A mixture of Phosphated Amine Oxide compounds as claimed in claim 2 of the formulas

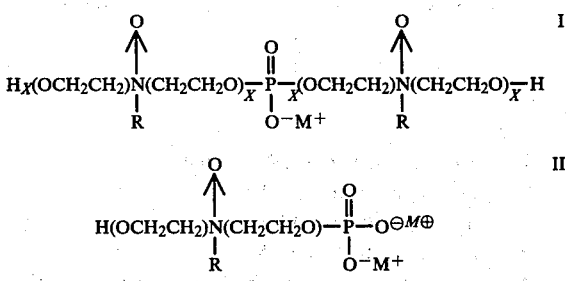

Wherein the ratio of I to II is from about 1 to 1; to about 1 to 2.

6. A mixture as claimed in claim 5 wherein R has a coco alkyl distribution.

7. A mixture as claimed in claim 5 wherein R has a tallow alkyl distribution.

8. A phosphated amine oxides produced by the process comprising reacting about one mole of compound I

Wherein
R and R', which may be the same or different and are selected from alkyl, alkenyl or alkoxy groups containing from about 5 to 24 carbon atoms, said R and R' may also be attached together to form cyclic structures
R' may be further selected from the same group as X with the requirement that said R' terminate in a hydroxyl group
X is a polyalkoxide of the formula

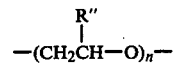

Wherein
R'' is hydrogen, $C_1$-$C_{20}$ alkyl, $C_1$-$C_{20}$ alkoxy or phenyl, n is an integer from 1 to 50 with about one mole of phosphorus pentoxide, neutralizing the resulting product with an aqueous base selected from the alkali and alkaline earth hydroxides and carbonates, and quaternary ammonium hydroxides so that the resulting mixture is between pH 7 to 9 and treating said mixture with about 1.1 moles of 35% hydrogen peroxide.

9. The product produced by the process as claimed in claim 8 wherein said compound I has the following formula

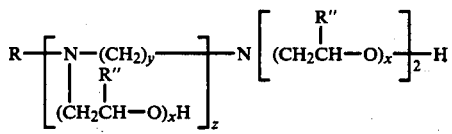

Wherein
R and R'' are as previously defined
Z is an integer from 1 to 10
Y is an integer from 2 to 10
X is an integer from 1 to 50.

10. The product produced by the process as claimed in claim 9 where said compound I is selected from 3 to 50 mole polyethoxylated fatty amino propylamines in which said fatty chains are derived from $C_5$ to $C_{24}$ carbon atoms.

11. The product produced by the process as claimed in claim 10 wherein said compound I is selected from 3 to 50 mole polyethoxylated tallow fatty amino propylamines.

12. The product produced by the process as claimed in claim 8 wherein said compound I has the following formula

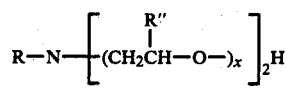

Wherein
R and R'' are as previously defined
X is an integer from 1 to 50.

13. The product produced by the process as claimed in claim 12 wherein said compound I is selected from 2 to 50 mole polyethoxylated fatty amines in which said fatty chains are derived from $C_8$ to $C_{24}$ carbon atoms.

14. The product produced by the process as claimed in claim 13 wherein said compound I is selected from 2 to 50 mole polyethoxylated coco amines.

15. The product produced by the process as claimed in claim 8 wherein said compound I is selected from 2 to 50 mole polyethoxylated tallow amines.

* * * * *

UNITED STATES PATENT AND TRADEMARK OFFICE
CERTIFICATE OF CORRECTION

PATENT NO. : 4,395,373
DATED : July 26, 1983
INVENTOR(S) : Robert B. Login

It is certified that error appears in the above-identified patent and that said Letters Patent are hereby corrected as shown below:

In the Specification, column 3, at the bottom of the page, the formula should read as follows:

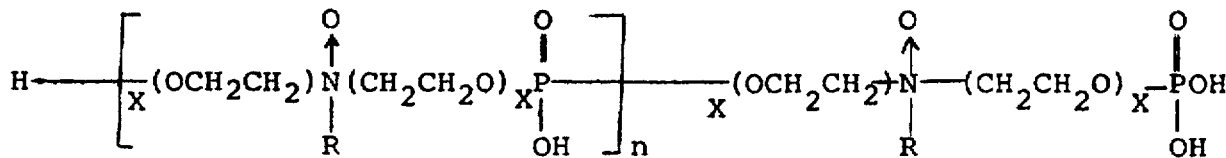

Signed and Sealed this

Twentieth Day of December 1983

|SEAL|

Attest:

GERALD J. MOSSINGHOFF

Attesting Officer  Commissioner of Patents and Trademarks